United States Patent [19]

Kwon

[11] 4,342,703

[45] Aug. 3, 1982

[54] PRODUCTION OF ALKYL HYPOHALITES

[75] Inventor: Joon T. Kwon, Freehold Township, Monmouth County, N.J.

[73] Assignee: The Lummus Company, Bloomfield, N.J.

[21] Appl. No.: 185,337

[22] Filed: Sep. 8, 1980

[51] Int. Cl.³ .............................................. C07C 69/63
[52] U.S. Cl. ........................................... 260/453 R X
[58] Field of Search ................................ 260/453 R X

[56] References Cited

U.S. PATENT DOCUMENTS 1,938,175 12/1933 Deanesly ..................... 260/453 R X
3,957,442 5/1976 Yamamoto et al. ................. 422/224
4,008,133 2/1977 Gelbein et al. ............. 260/453 R X Primary Examiner—John M. Ford
Assistant Examiner—Robert C. Whittenbaugh
Attorney, Agent, or Firm—Elliot M. Olstein; Louis E. Marn

[57] ABSTRACT

Alkyl hypohalites are produced by reaction of tertiary alkanol with chlorine and aqueous base, or pre-chlorinated aqueous base, in a high back-mix recycle loop reactor operated at a recycle ratio of at least 5:1 to thereby control reaction temperature and permit the use of short reaction times; i.e., less than 5 minutes. The loop reactor is operated at a velocity sufficient to maintain a well dispersed reaction mixture of the organic, aqueous and gas phases.

Tertiary butyl hypochlorite is a preferred product.

18 Claims, 1 Drawing Figure

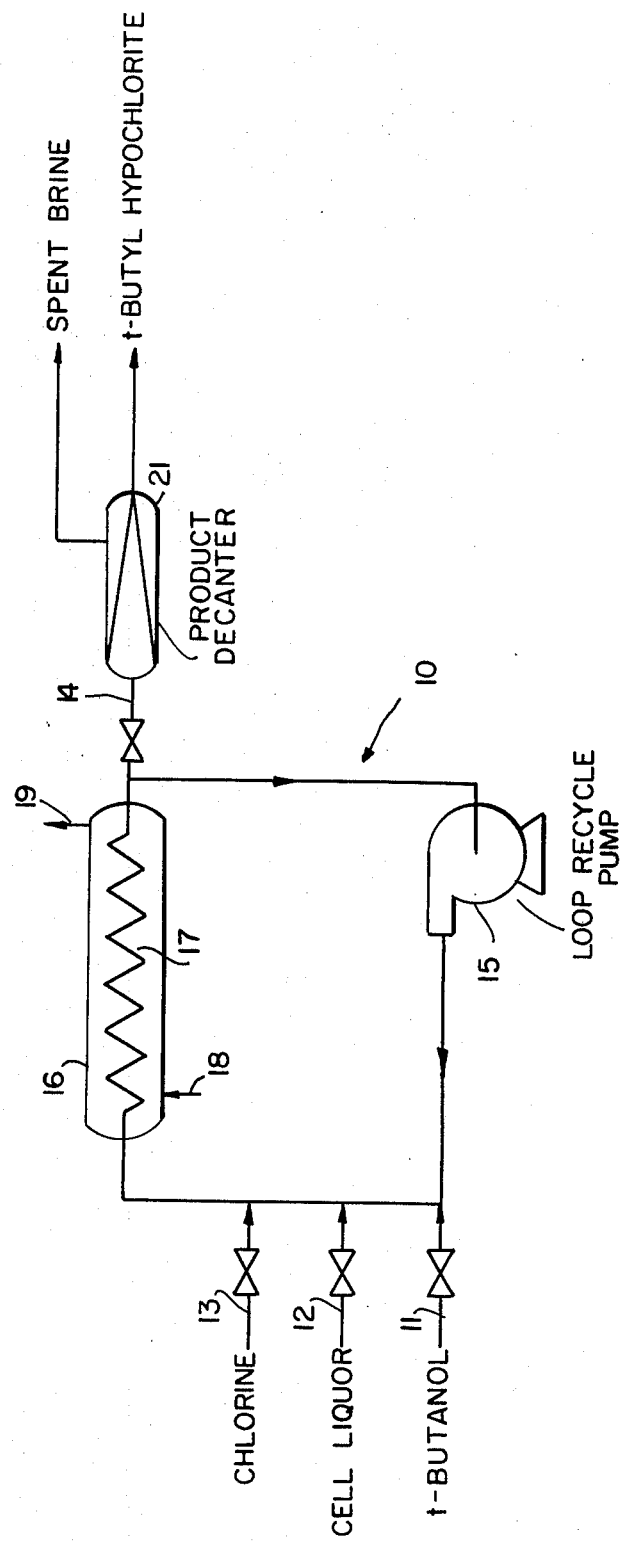

PRODUCTION OF ALKYL HYPOHALITES

This invention relates to the production of tertiary alkyl hypohalites, and more particularly to the production of tertiary alkyl hypochlorites.

The production of tertiary alkyl hypohalites, and in particular tertiary butyl hypochlorite by reaction of chlorine, aqueous base and tertiary alkanol is generally known in the art, e.g., U.S. Pat. No. 1,938,175 and U.S. Pat. No. 3,149,140.

U.S. Pat. No. 4,008,133 discloses the production of a tertiary alkyl hypochlorite by reaction of chlorine, aqueous base and tertiary alkanol for use in a process for producing olefin oxides wherein the tertiary alkyl hypochlorite is employed for producing chlorohydrin from olefin, with the chlorohydrin subsequently being saponified to the olefin oxide.

The reaction for producing tertiary alkyl hypohalite is a highly exothermic reaction, and as a result, it is necessary to control reaction temperature in order to prevent a runaway exotherm, which could result in a possible explosion as a result of the thermal instability of tertiary alkyl hypohalite.

The present invention is directed to a new and improved process for producing tertiary alkyl hypohalites.

In accordance with the present invention, tertiary alkyl hypohalite is produced by reaction of tertiary alkanol with (1) halogen, and an aqueous inorganic base, and/or (2) prehalogenated aqueous inorganic base, with the reaction being conducted in a high back-mix recycle loop reactor at a temperature of no greater than 100° C., and at a recycle ratio of at least 5:1 to thereby produce the tertiary alkyl hypohalite as product. In this manner, it is possible to prevent a runaway exotherm, and to produce the tertiary alkyl hypohalite in reaction times of no greater than 5 minutes.

More particularly, the tertiary alkyl hypohalite is produced in a reaction loop operated at a high back-mix rate and a velocity whereby the reaction mixture is uniformly mixed throughout the reactor, i.e., there is essentially no separation of the gas, hypochlorite and aqueous phases into separate flow regimes. The exothermic heat of reaction is removed by suitable cooling of the reactor loop; for example, in a constant temperature bath or by use of a circulating liquid through an external jacket. By employing a recycle rate of at least 5:1, as hereinabove described, it is possible to effectively remove the exothermic heat of reaction to control the temperature to no greater than 100° C., and permit the use of reaction times of no greater than 5 minutes.

The reaction temperature is controlled to no greater than 100° C., preferably no greater than 80° C., and in general, the reaction temperature is in the order of from 0° C. to 60° C., and preferably 30° C. to 50° C. The reaction pressure may vary from 0 psig to 50 psig, and is preferably in the order of from 5 psig to 20 psig. The recycle rate is at least 5:1, and in general does not exceed 60:1. In most cases, the recycle rate is preferably 10:1 to 40:1. The recycle rate is by volume based on combined feed.

Although the present invention is generally applicable to the production of tertiary alkyl hypohalites, including hypochlorites, hypobromites, and hypoiodites, the present invention is of particular applicability to the production of hypochlorites, and preferably to the production of tertiary butyl or tertiary amyl hypochlorite. The invention will be further described with respect to the production of tertiary butyl hypochlorite; however, it is to be understood that the following description is equally applicable to the production of other hypohalites.

The aqueous inorganic base is generally an alkali metal or alkaline earth metal hydroxide, with sodium, potassium and calcium hydroxide being preferred. The mole ratio of chlorine to tertiary alkanol is generally in the order of from 0.8:1 to 2.0:1, and preferably in the order of from 1.00:1 to 1.10:1. The ratio of base to tertiary alkanol is generally in the order of from 0.8:1 to 1.2:1, and preferably from 1.00:1 to 1.02:1. The selection of optimum amounts is deemed to be within the scope of those skilled in the art from the teachings herein.

In accordance with the present invention, the aqueous base may be prechlorinated to produce the alkali hypochlorite, and the prechlorinated aqueous base introduced into the loop reactor for reaction with the tertiary alkanol. Thus, in accordance with the present invention, the hypochlorite may be produced by either directly reacting chlorine, aqueous inorganic base and tertiary alkanol, or by reacting the tertiary alkanol with a prechlorinated aqueous base.

The present invention has particular applicability to a process for producing olefin oxide wherein tertiary alkyl hypochlorite is produced for subsequent reaction with olefin, as described, for example, in U.S. Pat. No. 4,008,133. In accordance with such a process, aqueous electrolyte derived from the cathode compartment of an electrolytic cell for producing chlorine, which contains sodium hydroxide and sodium chloride, is introduced into the high back-mix recycle loop reactor along with chlorine generated in the cell and tertiary alkanol to produce tertiary alkyl hypochlorite, as hereinabove described. Alternatively, all or a portion of such electrolyte may be prechlorinated with chlorine from the cell, and the prechlorinated aqueous electrolyte introduced into the loop reactor along with tertiary alkanol and remaining chlorine requirements, if any, to produce the tertiary alkyl hypochlorite, as hereinabove described. The aqueous brine, generated as byproduct, is recycled to the electrolytic cell, after appropriate treatment, if required, to remove any organic impurities. In accordance with such an embodiment, it is preferred to employ a slight stochiometric excess of base and chlorine to insure reaction of essentially all of the tertiary alkanol, with the chlorine requirements not being too far in excess in order to prevent excess chlorine in the reaction product. In general, the chlorine to tertiary alkanol mole ratio is from 0.8 to 2.0:1 and the sodium hydroxide to tertiary alkanol molar ratio is from 0.8 to 1.2:1.

The process of the present invention is also applicable to the production of hypochlorite in the presence of an inert organic solvent, as described in U.S. Application Ser. No. 35,558, filed on May 3, 1979, and U.S. Application Ser. No. 35,557, filed May 3, 1979.

As described in such applications, there is provided an improved process for producing an epoxy compound from an olefinically unsaturated compound by employing a hypochlorite for converting olefin to chlorohydrin and subsequent saponification of the chlorohydrin to the epoxy compound wherein the hypochlorite production, chlorohydrin production and saponification are effected in the presence of an inert organic solvent to thereby effectively recover the organic components produced in such steps. In accordance with the present invention, it is possible to produce the hypochlorite in the high back-mix recycle loop reactor, as hereinabove described, in the presence of an inert (does not adversely affect the reaction) organic solvent, such as a chlorinated hydrocarbon (a chlorinated aromatic compound, a chlorinated paraffin, etc.); a ketone, and the like, or mixtures thereof.

Thus, in accordance with the present invention, hypochlorite is produced from a tertiary alkanol in a high back-mix recycle loop reactor at a maximum temperature of 100° C. and at a recycle ratio of at least 5:1, and such a process has particular applicability to the production of a hypochlorite as a precursor for production of chlorohydrin for subsequent production of olefin oxide.

The invention will be further described with respect to the accompanying drawing, wherein:

The drawing is a simplified schematic representation of a loop reactor for producing hypochlorites.

It is to be understood, however, that the scope of the invention is not limited to the drawing.

Referring now to the drawing, there is shown a recycle loop reactor, schematically generally indicated as 10, which is provided with an inlet 11 for introduction of tertiary alkanol; in particular, tertiary butanol, an inlet 12 for introduction of aqueous base; in particular cell liquor comprised of an aqueous solution of sodium hydroxide and sodium chloride, and an inlet 13 for introduction of gaseous chlorine. The loop reactor is further provided with an outlet 14 for withdrawal of reaction product.

As particularly shown, the loop reactor 10 includes a loop recyle pump 15 and a heat exchange jacket 16 which surrounds a coil portion 17 of the loop reactor 10. The jacket is provided with a suitable inlet 18 and a suitable outlet 19 for production and withdrawal, respectively, of a suitable heat transfer fluid for cooling material flowing through the coil portion 17 of the loop reactor 10.

The loop reactor 10 is operated as hereinabove described to provide a recycle rate of at least 5:1, and a velocity through the loop reactor to provide a uniform mixing of the reaction mixture; i.e., no separation into separate flow regimes. In addition, the overall operation is coordinated so that sufficient heat is removed in the jacket 16 to maintain the reaction temperature in the loop reactor at no greater than 100° C., and preferably at no greater than 80° C. In addition, the operation is conducted in a manner such that the reaction time is preferably no greater than 5 minutes.

In operation, the chlorine, cell liquor and tertiary butanol are introduced into the loop reactor 10 through inlets 13, 12 and 11, respectively, and flow through the loop reactor in a continuous loop, as a uniform mixture to produce tertiary butyl hypochlorite. Reaction product is withdrawn from the loop reactor 10 through line 14, with the rate of withdrawal being such that there is provided a recycle rate of at least 5:1, as hereinabove described.

The reaction product in line 14 is introduced into a suitable product decanter, schematically indicated as 21 to separate an aqueous brine phase from an organic phase of the tertiary butyl hypochlorite.

The loop reactor 10 may be provided with suitable static mixing means in order to improve contact between the reactants, and such static mixing means may be in the form of inserts, packing, and the like.

The present invention will be still further described with respect to the following example; however, the scope of the invention is not to be limited thereby:

EXAMPLE 1

The reactor was made of ¼" titanium and glass tubings, at a total volume of 111 cc. The aqueous feed was a prechlorinated cell liquor stream containing 8.423 wt% NaClO, 0.212 wt% NaOH and 18.640 wt% NaCl. The organic feed was a 10.75 wt% solution of t-butyl alcohol in carbon tetrachloride, in which 8.40 wt% of chlorine was dissolved upstream of the reactor. Reaction conditions and test results are as follows (temperature =40° C.):

| | |
|---|---|
| Reaction Time Based on Combined Product Volume (min.) | 1.80 |
| Reaction Time Based on Combined Feed Volume (min.) | 1.90 |
| Recycle/Combined Feed Vol. Ratio | 14/1 |
| Feed Mol Ratio (t-BuOH = 1.000) | |
| Chlorine | 1.031 |
| Caustic | 1.015 |
| Weight Accountability (%) | 102.84 |
| Chlorine Accountability (mol %) | 98.39 |
| t-BuOCl Yields (mol %) | |
| per t-BuOH Charged | 96.29 |
| per $Cl_2$ used | 99.88 |
| per NaOH Used | 103.84 |
| $Cl_2$ (org.)/($Cl_2$ + t-BuOCl) org., mol % | 5.72 |
| $Cl^+$ (aq.)/$Cl^+$ org. + $Cl^+$ aq.), mol % | 1.09 |

EXAMPLE 2

In the same reactor chlorine, cell liquor and t-butyl alcohol were charged together, at 49°±1° C./1 atm., to effect the chlorination in obtaining neat t-butyl hypochlorite. The cell liquor contained 8.66 wt% caustic. Reaction conditions and test results are as follows:

| | |
|---|---|
| Reaction Time Based on Combined Product Volume (min.) | 1.89 |
| Reaction Time Based on Combined Feed Volume (min.) | 2.07 |
| Recycle/Combined Feed Vol. Ratio | 15/1 |
| Feed Mol Ratio (t-BuOH = 1.000) | |
| Chlorine | 1.064 |
| Caustic | 1.014 |
| Weight Accountability (%) | 102.56 |
| Chlorine Accountability (mol %) | 92.11 |
| t-BuOCl Yields (mol %) | |
| per t-BuOH Used | 93.06 |
| per $Cl_2$ Used | 94.97 |
| per NaOH Used | 92.30 |
| $Cl_2$ (org.)/($Cl_2$ + t-BuOCl) org., mol % | 4.92 |
| $Cl^+$ (aq.)/($Cl^+$ org. + $Cl^+$ aq.), mol % | 0.13 |

The present invention is particularly advantageous in that tertiary alkyl hypohalites can be produced with effective temperature control to prevent a runaway exotherm. In addition, the hypochlorite may be produced at shorter and more economical reaction times. The recycle loop reactor, as hereinabove described, provides for uniform mixing of reactants through the system; precise and uniform reaction temperature and pressure; little or no chance of phase separation into separate flow regimes throughout the reactor, and little or no scale up difficulties.

Numerous modifications and variations of the present invention are possible in light of the above teachings and, therefore, within the scope of the appended claims, the invention may be practised otherwise than as particularly described.

I claim:

1. In a process for producing a tertiary alkyl hypohalite, by reacting tertiary alkanol with at least one member selected from the group consisting of (a) halogen and aqueous inorganic base and (b) aqueous inorganic base which has been reacted with a halogen, the improvement comprising:

reacting the tertiary alkanol with said at least one member in a cooled high back-mix recycle loop reactor flow at a recycle ratio of at least 5:1 to produce the tertiary alkyl hypohalite in a reaction time of no greater than 5 minutes at a reaction temperature of no greater than 100° C. and at a velocity to provide a uniform mixing of the reactants in the loop reactor to provide a single phase flow regime.

2. The process of claim 1 wherein the halogen is chlorine.

3. The process of claim 2 wherein the tertiary alkanol is tertiary butanol, and the reaction product is tertiary butyl hypochlorite.

4. The process of claim 2 wherein the tertiary alkanol is reacted with chlorine and aqueous inorganic base.

5. The process of claim 4 wherein the recycle rate is from 10:1 to 40:1.

6. The process of claim 5 wherein the temperature is no greater than 80° C.

7. The process of claim 6 wherein the tertiary alkanol is reacted with chlorine and aqueous organic base in the presence of an inert organic solvent.

8. The process of claim 6 wherein the aqueous organic base is selected from the group consisting of alkali metal and alkaline earth metal hydroxides.

9. The process of claim 8 wherein the mole ratio of chlorine to tertiary alkanol is from 1.00:1 to 1.10:1 and the mole ratio of base to tertiary alkanol is from 0.8:1 to 1.2:1.

10. The process of claim 9 wherein the tertiary alkanol is tertiary butanol.

11. The process of claim 10 wherein the base is sodium hydroxide.

12. The process of claim 10 wherein the base is calcium hydroxide.

13. The process of claim 6 wherein the tertiary alkanol is reacted with prechlorinated aqueous inorganic base.

14. The process of claim 13 wherein the aqueous inorganic base is selected from the group consisting of alkali metal and alkaline earth metal hydroxides.

15. The process of claim 14 wherein the mole ratio of chlorine to tertiary alkanol is from 1.00:1 to 1.10:1 and the mole ratio of base to tertiary alkanol is from 0.8:1 to 1.2:1.

16. The process of claim 15 wherein the tertiary alkanol is tertiary butanol.

17. The process of claim 16 wherein the base is sodium hydroxide.

18. The process of claim 16 wherein the base is calcium hydroxide.

* * * * *